United States Patent

Meyer et al.

Patent Number: 6,099,751
Date of Patent: Aug. 8, 2000

[54] CHIRAL COMPOUNDS

[75] Inventors: Frank Meyer, Mannheim; Karl Siemensmeyer, Frankenthal; Hans-Georg Kuball, Stelzenberg; Bernhard Weiss, Kaiserslautern, all of Germany; Dieter Seebach, Zürich, Switzerland

[73] Assignee: BASF Aktiengesellschaft, Ludwigshafen, Germany

[21] Appl. No.: 09/142,257

[22] PCT Filed: Mar. 7, 1997

[86] PCT No.: PCT/EP97/01163

§ 371 Date: Sep. 18, 1997

§ 102(e) Date: Sep. 18, 1998

[87] PCT Pub. No.: WO97/34886

PCT Pub. Date: Sep. 25, 1997

[30] Foreign Application Priority Data

Mar. 21, 1996 [DE] Germany .......................... 196 11 101

[51] Int. Cl.[7] .......................... C09K 19/34; C09K 19/58; C07D 307/00
[52] U.S. Cl. .................. 252/299.61; 252/299.2; 549/430
[58] Field of Search ............................ 252/299.61, 299.2; 549/430

[56] References Cited

U.S. PATENT DOCUMENTS

| | | | |
|---|---|---|---|
| 5,047,557 | 9/1991 | Hafner et al. | 549/206 |
| 5,498,367 | 3/1996 | Buchecker et al. | 252/299.61 |

FOREIGN PATENT DOCUMENTS

| | | |
|---|---|---|
| 0 233 602 | 8/1987 | European Pat. Off. . |
| 0 261 712 | 8/1987 | European Pat. Off. . |
| 0 387 196 | 9/1990 | European Pat. Off. . |
| 43 42 280 | 6/1995 | Germany . |
| 195 32 408 | 9/1995 | Germany . |
| 196 02 795 | 1/1996 | Germany . |
| 196 02 848 | 1/1996 | Germany . |
| WO 93/05436 | 3/1993 | WIPO . |

OTHER PUBLICATIONS

Helvetica Chimica ACTA, vol. 79, 9, Sep. 18, 1996.
Journal of the American Chemical Society, vol. 114, No. 7, Mar. 25, 1992, DC US, pp. 2321–2336.
Encyclopedia of Regents for Organic Synthesis, Paquette, L.A., Ed., John Wiley & Sons, Chichester, 1995, Dahinder, et al.
The Journal of Organic Chemistry, vol. 60, Mar. 24, 1995, No. 6, 1788–1799, Dahinden et al.
Berichte der Bunsen–Gesellschaft Fur Physikalische Chemie, phys. Chem. 78, (1974), 869.

*Primary Examiner*—C. H. Kelly
*Attorney, Agent, or Firm*—Oblon, Spivak, McClelland, Maier & Neustadt, P.C.

[57] ABSTRACT

Chiral compounds of the formula I

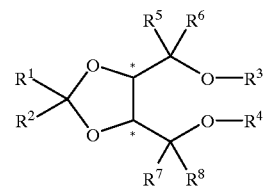

where:
$R^1, R^2, R^3, R^4$ are hydrogen or aromatic, aliphatic or araliphatic radicals having 1 to 40 carbon atoms,
$R^5, R^6, R^7, R^8$ are aromatic or aliphatic radicals having 1 to 20 carbon atoms,
with the proviso that at least one of the radicals $R^1$ to $R^8$ contains a polymerizable group,
are used as dopes in liquid crystals, in compositions for coating substrates and in the preparation of interference pigments which can be used in printing inks and surface coatings.

9 Claims, No Drawings

CHIRAL COMPOUNDS

The present invention relates to chiral compounds of the formula I

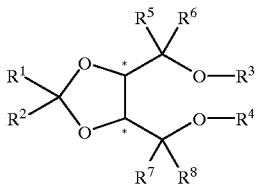

where
R$^1$,R$^2$,R$^3$ and R$^4$ are hydrogen or aromatic, aliphatic or araliphatic radicals having 1 to 40 carbon atoms,
R$^5$,R$^6$,R$^7$ and R$^8$ are aromatic or aliphatic radicals having 1 to 20 carbon atoms,
with the proviso that at least one of the radicals R$^1$ to R$^8$ contains a polymerizable group.

The invention furthermore relates to the use of chiral compounds of the formula Ia

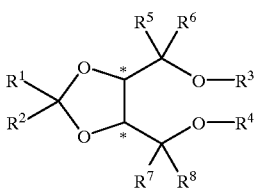

where
R$^1$,R$^2$,R$^3$ and R$^4$ are hydrogen or aromatic, aliphatic or araliphatic radicals having 1 to 40 carbon atoms,
R$^5$,R$^6$,R$^7$ and R$^8$ are aromatic or aliphatic radicals having 1 to 20 carbon atoms,
to liquid-crystalline compositions containing the chiral compounds, to the use of these liquid-crystalline compositions for coating substrates and for the preparation of interference pigments, and to the use of the interference pigments in printing inks and surface coatings.

Chiral compounds of formula Ia where R$^3$ and R$^4$ are hydrogen, and R$^5$ and R$^6$ are aryl has been known for some time under the name TADDOLs (α,α,α',α'-tetraaryl-1,3-dioxolane-4,5-dimethanols) and are used, for example, as catalysts for enantioselective syntheses. (cf. Dahinden et al. in "Encyclopedia of Reagents for Organic Synthesis", Paquette, L. A., Ed.; John Wiley & Sons, Chichester, 1995).

Liquid-crystalline phases containing chiral compounds frequently have remarkable properties. Thus, cholesteric phases, in which the molecule of the liquid-crystalline compound has a helical arrangement, can be formed, for example, by doping a nematic liquid-crystalline phase with a chiral compound. Such cholesteric phases frequently exhibit colored interference effects through selective reflection of light of a certain wavelength at the helical liquid-crystal structure. These colored cholesteric phases can be frozen, for example by cooling to below the glass transition temperature or by incorporation into polymeric networks, enabling their use in colored coatings or as interference pigments.

Numerous compounds have been disclosed as chiral dopes for liquid-crystalline phases (for example in DE-A 4342280). Suitable dopes should have a high twisting power, so that small amounts of the dope are sufficient to induce the helical structure. In addition, the chiral dopes should have good compatibility with the liquid-crystalline compounds, enabling effective interaction between these components. Many of the known chiral dopes are unsatisfactory with respect to these properties. In addition, many chiral compounds are of only limited suitability for polymeric cholesteric liquid-crystal systems, since they cannot be incorporated covalently into polymeric networks.

It is an object of the present invention to provide chiral compounds which are highly suitable as dopes for liquid crystals owing to their compatibility with liquid-crystalline compounds and their twisting power.

We have found that this object is achieved by the chiral compounds of the formulae I and Ia mentioned at the outset.

In the formulae I and Ia, the radicals R$^5$, R$^6$, R$^7$ and R$^8$ are aromatic or aliphatic radicals having 1 to 20 carbon atoms. These radicals are preferably sterically hindered radicals, since their size has a particular effect on the twisting power of the compounds. First, at least one of the radicals in the pairs R$^5$/R$^6$ and R$^7$/R$^8$ is preferably a branched or cyclic aliphatic radical having 6–20 carbon atoms. The volume of the substituents is more important here than the chemical composition. Thus, besides pure hydrocarbon radicals, alkyl or cycloalkyl groups which are interrupted by oxygen, sulfur, imino or C$_1$–C$_4$-alkylimino groups are also suitable. Examples of hydrocarbon radicals which may be mentioned are methyl, ethyl, isopropyl, n-propyl, n-butyl, isobutyl, sec-butyl, tert-butyl, n-pentyl, isopentyl, neopentyl, tert-pentyl, and preferably branched hexyl, heptyl, octyl, nonyl, decyl, undecyl, dodecyl, tridecyl, tetradecyl, hexadecyl, octadecyl and eicosyl. Cycloaliphatic radicals, such as cyclopentyl, cyclohexyl, cycloheptyl and decahydronaphthyl, are also suitable.

R$^5$, R$^6$, R$^7$ and R$^8$ are particularly preferably aromatic radicals, in particular phenyl and naphthyl radicals. Owing to their easier availability, unsubstituted phenyl and naphthyl radicals are preferred, but it is also possible to use phenyl and naphthyl radicals which are substituted, for example, by C$_1$–C$_4$-alkyl radicals from the abovementioned group. Particularly preferred substituents for the phenyl and naphthyl radicals are vinyl and vinyloxy radicals, the chiral compounds can be fixed in polymeric liquid crystals via these polymerizable groups. Other suitable substituents for the phenyl and naphthyl radicals are hydroxyl groups, which can be reacted, for example, with acrylic acid or methacrylic acid to give the corresponding esters, thus enabling introduction of a polymerizable group after synthesis of a compound of the formula I or Ia.

The radicals R$^1$, R$^2$, R$^3$ and R$^4$ have less influence on the twisting power than do the radicals R$^5$, R$^6$, R$^7$ and R$^8$, but affect, in particular, the compatibility with the liquid-crystalline host systems. For this reason, their chemical properties are more important than their volume. Similarity of at least some of the radicals R$^1$ to R$^4$ with the chemical structures of liquid-crystalline compounds is frequently advantageous. This gives good solubility in the liquid-crystal phase and strong interactions, which in turn results in more effective twisting of the liquid-crystal phase. Owing to the multiplicity of possible liquid-crystalline host systems, a multiplicity of different structures for the radicals R$^1$ to R$^4$ is therefore also possible.

Besides hydrogen, the radicals R$^1$ and R$^2$ can also be a wide variety of aromatic, aliphatic or araliphatic radicals. Depending on whether the dioxolane ring system with the radicals R$^1$ and R$^2$ in the 2-position is formed by acetalation or ketalation, the two radicals can both be organic radicals or one of the radicals can be hydrogen, this latter possibility being preferred. Suitable aliphatic radicals $R^1$ and/or $R^2$ are, for example, the $C_1$–$C_{20}$-alkyl radicals mentioned above for $R^5$ to $R^8$. Non-adjacent $CH_2$ groups in these alkyl radicals may be replaced by oxygen, sulfur or $C_1$–$C_4$-alkylimino. Of these simple aliphatic radicals, particular mention should be made of the methyl radical.

Suitable radicals $R^1$ and/or $R^2$ are furthermore aromatic radicals, such as phenyl or substituted phenyl radicals. The substituents on the phenyl radicals can be, for example, the abovementioned $C_1$–$C_{20}$-alkyl radicals, which may be interrupted by oxygen, sulfur or $C_1$–$C_4$-alkylimino, corresponding $C_1$–$C_{20}$-alkoxy radicals or halogen, such as chlorine or bromine, or the cyano radical. Preferred substituents are again polymerizable radicals, such as vinyl, vinyloxy, acryloxy or methacryloxy.

Preferred radicals $R^1$ and $R^2$ are those of the formula

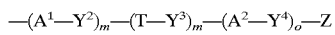

where

Y$^2$, Y$^3$ and Y$^4$ are a single covalent bond, oxygen, sulfur, —CO—O—, —O—CO—, —O—CO—O—, —CO—NR$^9$— or —NR$^9$—CO—, where these bridges may be identical or different, A$^1$ and A$^2$ are identical or different alkylene radicals having 2 to 12 carbon atoms, in which non-terminal, non-adjacent CH$_2$ groups may be replaced by oxygen, T are identical or different aliphatic or aromatic rings, which may contain up to 3 hetero atoms, R$^9$ is hydrogen or $C_1$–$C_4$-alkyl, m and o are 0 or 1, n is 0, 1, 2, 3 or 4 and z is hydrogen or a polymerizable radical.

Preferred bridges Y$^2$, Y$^3$ and Y$^4$ are —CO—O—, —O—CO— and —O—CO—O— besides the direct bond. Examples of spacers A$^1$ and A$^2$ are the —(CH$_2$)$_r$— and —(CH$_2$CH$_2$O)$_s$—CH$_2$CH$_2$— groups, where r is from 1 to 12, and s is from 1 to 3.

The radicals T can be, for example, fluorine-, chlorine-, bromine-, cyano-, hydroxyl- or nitro-substituted ring systems. Preferred radicals T are the following:

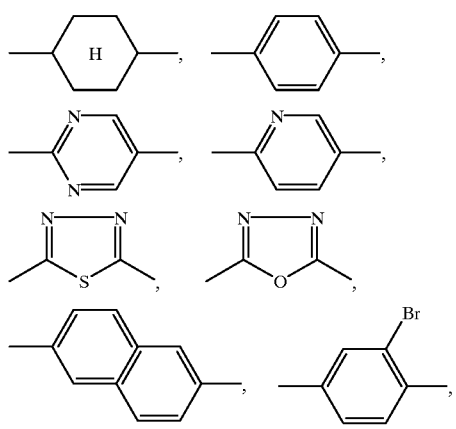

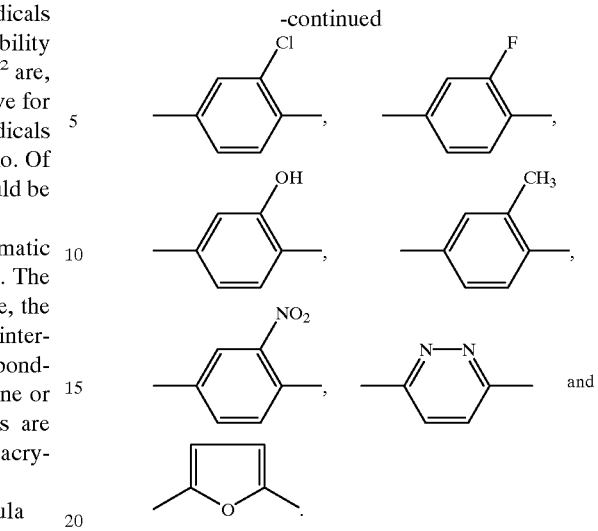

Particular preference is given the following moieties (T—Y$^3$)$_n$:

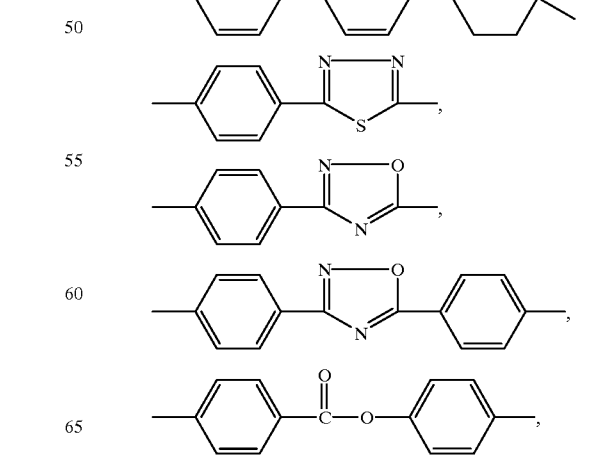

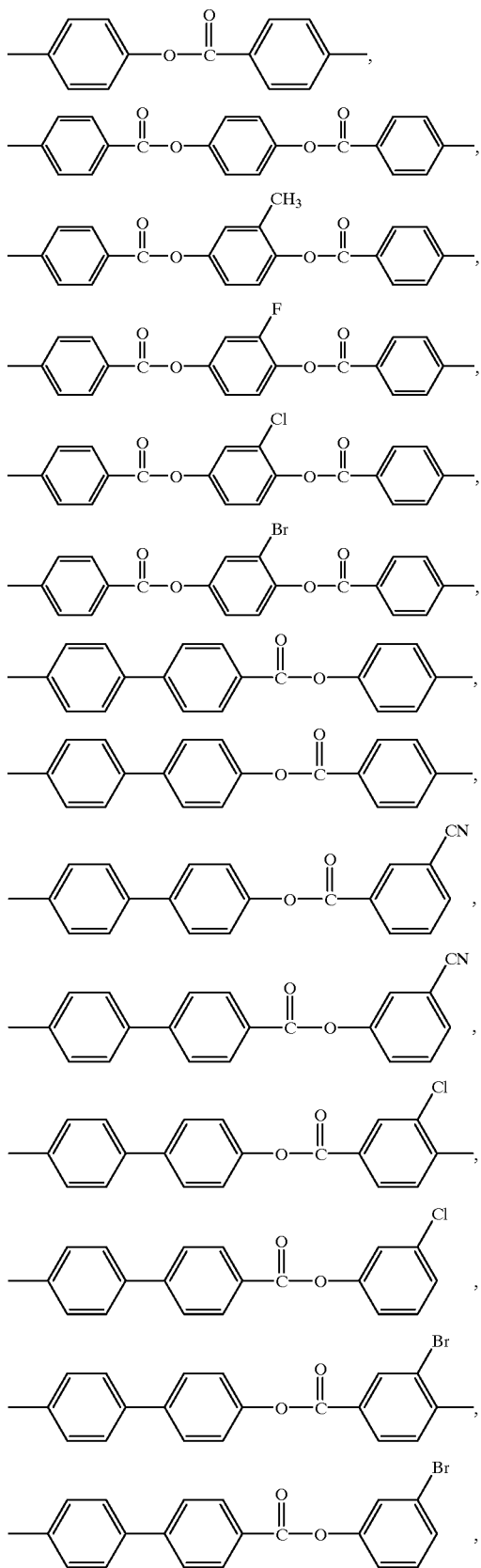

and

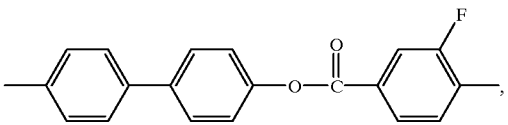

Besides hydrogen, $R^9$ can be methyl, ethyl, propyl or butyl.

m and o are preferably 1, and n is preferably 2 or 3.

Besides hydrogen, the radicals Z can also be polymerizable radicals. Examples of preferred polymerizable radicals are

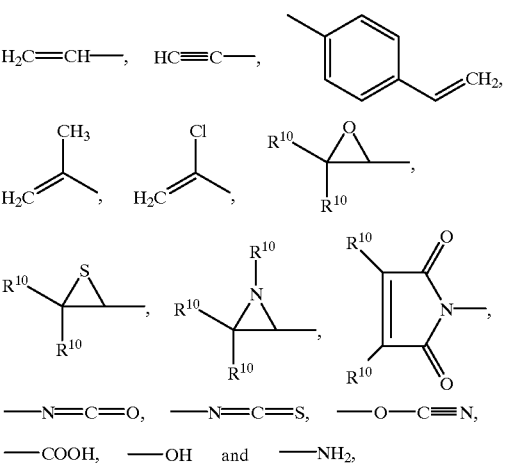

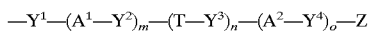

—COOH, —OH and —NH$_2$, where the radicals $R^{10}$ can be identical or different and are hydrogen or $C_1$–$C_4$-alkyl, such as methyl, ethyl, propyl, isopropyl, n-butyl, isobutyl, sec-butyl or tert-butyl.

It should be noted here that, in the case of polymerizable radicals bonded via heteroatoms, the bonding must take place to a carbon atom, i.e. $Y^4$ must in these cases be a direct bond.

Preferred groups $Y^4$—Z are acryloxy, methacryloxy, vinyl, vinyloxy, styryl and styryloxy.

The radicals $R^3$ and $R^4$ are preferably hydrogen, in particular if $R^5$ to $R^8$ are very bulky radicals. In order to increase the compatibility with liquid-crystalline compounds, the radicals $R^3$ and/or $R^4$ can, however, also be radicals containing the structural features mentioned for $R^1$ and $R^2$. Essentially the same preferences apply here as already mentioned for $R^1$ and $R^2$. In particular, suitable radicals $R^3$ and $R^4$ are those of the formula —Y$^1$—(A$^1$—Y$^2$)$_m$—(T—Y$^3$)$_n$—(A$^2$—Y$^4$)$_o$—Z where the variables are as defined above, and $Y^1$ is a single covalent bond, —CO— or —CO—O—.

Essentially the abovementioned preferences apply to these variables.

The preparation of TADDOLs is known per se, for example from D. Seebach et al., J. Org. Chem. 60, (1995), 1788. In order to prepare the compounds I and Ia, the same synthetic routes can be selected as for the known TADDOLS. In general, the starting materials are methyl tartrates. In the first step, the 1,3-dioxolane ring is usually formed by reaction with the desired aldehyde or ketone of the formula $R^1$—CO—$R^2$.

The preferred moieties of the formula

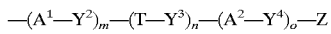

can be obtained in a known manner by conventional condensation reactions, known to the person skilled in the art, of the elements $A^1/A^2$ with $T$—$(Y^3$—$T)_{n-1}$ or $Z$, with formation of the other bridges $Y^2$ and $Y^4$. Such reactions are described, for example, in the earlier German patent application 19532408.0.

The substituents $R^5$, $R^6$, $R^7$ and $R^8$ can then be obtained by reaction with Grignard compounds of the formula $R^5$MgBr. If $R^5$ to $R^8$ are different radicals, the reaction is initially carried out with a relatively small amount (for example a molar ratio of 4:1) of Grignard compounds, the monosubstituted product is purified, and then reacted successively with the other Grignard compounds. After the Grignard reactions, the compounds I or Ia where $R^3$ and $R^4$ are hydrogen are thus obtained.

Other radicals $R^3$ and/or $R^4$ are obtained, for example, by known methods of ether synthesis, for example by reaction with halogen-$R^3$ compounds or by reaction with acid halides or halocarbonic esters, depending on whether the variable $Y^1$ in the preferred radicals of the formula —$Y^1$—$(A^1$—$Y^2)_m$—$(T$—$Y^3)_n$—$(A^2$—$Y^4)_o$—$Z$ is a single covalent bond, a carbonyl group or an oxycarbonyl group.

The polymerizable groups in the compounds of the formula I or Ia can be introduced either during the abovementioned process steps by reaction with compounds which already carry polymerizable substituents, or they can be introduced after these synthesis steps, for example by esterification of the hydroxyl groups in the corresponding radicals, for example using acrylic acid or methacrylic acid.

Novel liquid-crystalline compositions contain one or more chiral compounds of the formula I or Ia as dopes, usually in concentrations of from 0.1 to 10% by weight, based on the total amount of the liquid crystal. The concentration is selected so that the desired interference hue is formed. Higher concentrations shift the hue into the blue region, and lower ones shift it into the red region.

Particularly suitable liquid-crystalline compositions are those in which the achiral liquid-crystalline compounds are polymerizable compounds, since the cholesteric liquid-crystalline ordered state can be fixed in such compositions by polymerization. Suitable polymerizable liquid-crystalline compounds are described, for example, in WO 93/05436, EP-A 261 712 and in the earlier German patent application 19532408.0. Particularly stable systems are those in which the chiral dope of the formula I or Ia also contains at least one polymerizable group, since diffusion of the dope out of the liquid-crystalline ordered phase is thus prevented.

Said liquid-crystalline compositions can advantageously be used for coating substrates. Examples of suitable substrates are metal surfaces, plastic surfaces, glass or ceramic surfaces or films.

Furthermore, the novel liquid-crystalline compositions can be used for the preparation of interference pigments. To this end, the preferably polymerizable compositions are, for example, applied to a substrate, preferably glass or a smooth film, if desired by knife coating or other physical influences, and then polymerized. The polymerized liquid-crystal film is then detached from the substrate and comminuted to pigment-particle size. Further details on suitable pigment preparation processes are given in the earlier German patent applications 19 602 795.0 and 10 19 602 848.5. The predominantly platelet-shaped pigments formed can be used as effect pigments with a viewing-angle-dependent color impression in printing inks and surface coatings.

EXAMPLES

Example 1

Preparation of (4 S-trans)-2,2-dimethyl-α,α,α',α',-tetra(2-naphthyl)-α,α', -di-(acryloyloxymethyl)-1,3-dioxolane 0.5 g (0.75 mmol) of (4 S-trans)-2,2-dimethyl-α,α,α',α',-tetra(2-naphthyl)-1,3-dioxolane-4,5-dimethanol was dissolved in 40 ml of toluene. 0.15 g (1.5 mmol) of triethylamine and 0.34 g (3.75 mmol) of acryloyl chloride were added to the solution. The solution was stirred at 20° C. for 14 hours and then washed with water and dilute hydrochloric acid, the resultant precipitate was filtered off with suction, and the organic solution was dried over sodium sulfate. Purification was effected by column chromatography.

Yield: 0.36 g; $^1$H-NMR (CDCl$_3$): 0.95(s); 1.1(s); 4.1 (m); 5.05 (d); 5.6 (d); 5.95 (m); 6.1 (dd); 7.3–8.1 (m).

Helical Twisting Power (HTP): 27.3 $\mu m^{-1}$ (The HTP was determined by the method described by H. Finkelmann and H. Stegemeyer in Ber. Bunsengesellschaft Phys. Chem. 78, (1974), 869. The nematic host phase used was the liquid-crystal mixture ZLI 1840® from Merck, Darmstadt, Germany.)

Example 2

Preparation of (4 S-trans)-2,2-dimethyl-α,α,α', α',-tetra(2-naphthyl)-α,α',-di (acryloyloxybutyloxycarbonyloxy)-1,3-dioxolane Analogously to Example 1, 0.5 g (0.75 mmol) of (4 S-trans)-2,2-dimethyl-α,α,α',α',-tetra(2-naphthyl)-1,3-dioxolane-4,5-dimethanol was reacted with 0.77 g (3.75 mmol) of 4-(acryloyloxy)butyloxychloroformate, and the product was worked up.

Yield: 0.15 g; $^1$H-NMR (CDCl$_3$): 0.95 (s); 1.0 (s); 1.5 (bs); 3.87–3.90 (m) ; 4.05 (m); 5.05 (d); 5.6 (d); 5.95 (m); 6.1 (dd); 8.1–7.3 (m).

Helical Twisting Power (HTP): 37.5 $\mu m^{-1}$

We claim:

1. A chiral compound of the formula I

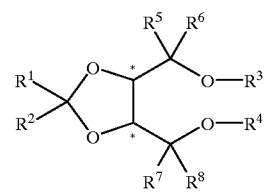

where $R^1$ and $R^2$ are hydrogen or aliphatic radicals having 1 to 40 carbon atoms, or aromatic or araliphatic radicals having 6 to 40 carbon atoms, $R^3$ and $R^4$ are aliphatic radicals having 1 to 40 carbon atoms, or aromatic or araliphatic radicals having 6 to 40 carbon atoms, $R^5$, $R^6$, $R^7$ and $R^8$ are aliphatic radicals having 1 to 20 carbon atoms, or aromatic radicals having 6 to 20 carbon atoms, with the proviso that at least one of the radicals $R^1$ to $R^8$ contains a polymerizable group.

2. A chiral compound of the formula I as claimed in claim 1, where $R^5$, $R^6$, $R^7$ and $R^8$ are unsubstituted or vinyl- or vinyloxy-substituted phenyl or naphthyl radicals.

3. A chiral compound of the formula I as claimed in claim 1, wherein $R^3$ and $R^4$ are,

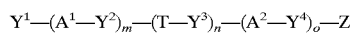

where $Y^1$ is a single covalent bond, —CO— or —CO—O—, $Y^2$, $Y^3$ and Y4, which are identical or different, are a single covalent bond, oxygen, sulfur, —CO—O—, —O—CO—, —O—CO—O—, —CO—$NR^9$— or —$NR^9$—CO—, $A^1$ and $A^2$ are identical or different alkylene radicals having 2 to 12 carbon atoms, in which non-terminal, non-adjacent $CH_2$ groups may be replaced by oxygen, T are identical or different aliphatic or aromatic rings, which may contain up to 3 hetero atoms, $R^9$ is hydrogen or $C_1$–$C_4$-alkyl, m and o are 0 or 1, n is 0, 1, 2, 3, or 4, and Z is hydrogen or a polymerizable radical.

4. A chiral compound of the formula I as claimed in claim 3, where $R^1$ and $R^2$, independently of one another are hydrogen or radicals of the formula —$(A^1—Y^2)_m$—$(T—Y^3)_n$—$(A^2—Y^4)_o$—Z.

5. A liquid-crystalline composition containing, as dope, one or more chiral compounds of the formula I as claimed in claim 1.

6. A liquid-crystalline composition as claimed in claim 5, containing polymerizable, achiral liquid-crystalline compounds in addition to the compounds of the formula I.

7. A coated substrate comprising the liquid-crystalline composition as claimed in claim 5.

8. An interference pigment comprising the liquid-crystalline composition as claimed in claim 5.

9. A printing ink or surface coating comprising the pigment as claimed in claim 8.

* * * * *

UNITED STATES PATENT AND TRADEMARK OFFICE
CERTIFICATE OF CORRECTION

PATENT NO. : 6,099,751
DATED : August 8, 2000
INVENTOR(S): Frank MEYER et al.

It is certified that an error appears in the above-identified patent and that said Letters Patent is hereby corrected as shown below:

On the title page, item [86] is incorrect. The PCT No. information should be:

--[86] PCT No.:     PCT/EP97/01163

§ 371 Date:    Sep. 18, 1998

§ 102(e) Date: Sep. 18, 1998--

Signed and Sealed this

Seventeenth Day of April, 2001

Attest:

NICHOLAS P. GODICI

Attesting Officer      Acting Director of the United States Patent and Trademark Office